(12) United States Patent
Lopatin (10) Patent No.: US 7,294,348 B2
(45) Date of Patent: Nov. 13, 2007

(54) POLYFUNCTIONAL BIOCOMPATIBLE HYDROGEL AND METHOD FOR THE PRODUCTION THEREOF

(75) Inventor: Vladislav Victorovich Lopatin, Moscow (RU)

(73) Assignee: Biopharma Development, Ltd., London (GB)

( * ) Notice: Subject to any disclaimer, the term of this patent is extended or adjusted under 35 U.S.C. 154(b) by 318 days.

(21) Appl. No.: 10/490,969

(22) PCT Filed: Sep. 28, 2001

(86) PCT No.: PCT/RU01/00392

§ 371 (c)(1),
(2), (4) Date: Mar. 25, 2004

(87) PCT Pub. No.: WO03/026711

PCT Pub. Date: Apr. 3, 2003

(65) Prior Publication Data

US 2004/0241241 A1    Dec. 2, 2004

(51) Int. Cl.
*A61K 9/14* (2006.01)
(52) U.S. Cl. .......................... 424/486; 524/916
(58) Field of Classification Search ................ 424/486; 525/916
See application file for complete search history.

(56) References Cited

FOREIGN PATENT DOCUMENTS

| EP | 0742022 A1 | 11/1996 |
| GB | 2114578 A | 8/1983 |
| RU | 2088234 C1 | 8/1997 |
| RU | 2127129 C1 * | 3/1999 |
| RU | 2146127 C1 * | 3/2000 |
| WO | WO 01/49336 A1 * | 7/2001 |

OTHER PUBLICATIONS

Lindemann et al, Jun. 1997, Macromolecules, 30, 4073-4077.*
A.B.Shekhter et al. "Injectable hydrophilic polyacrylamide gel Formacryl and tissue response to its implantation", in magazine "Records of Plastic, Reconstructive and Aesthetic Surgery", 1997, No. 2, p. 19.
Savitskaya M.N. Kholodova Y.D. "Polyacrylamide", Publishing House "Tekhnika", 1969, p. 103.
Other important inventions in the field of medicine:Antimicrobial agent Povyargolum. Dec. 5, 1999. http://horne.comset.net/poviarg/.
"Methodical Directions on Sanitary and Hygienic Evaluation of Rubber and Latex Devices, Meant for Medical Purposes", Moscow, 1988, pp. 18-19.
Methodic recommendations "Admissible amount of migration of chemical agents, that are exuded from polymer and other materials in contact with food hydrogels and methods of their determination" Sanitary Rules and Standards 42-122-42-40-86.
V. V. Kuznetsov et al. "Determination of Acrylamide in Polyacrylamidic gels", The 52-nd Pittsburgh Conference on Analytical Chemistry and Applied Spectroscopy. -New Orleans, LA, 2001, Abstract Book, No. 1648.
"Method for Determination of Microorganisms' Antibiotic Perceptibility by Disk Diffusion Technique", Moscow, Ministry of Public Health, 1984.
"Practical Work on Physical Chemistry", Moscow, 1974, pp. 86-97.
"Collected Guide Materials On Toxicological Examination of Polymeric Materials and Devices for Medical Purposes, Made on Their Bases", Moscow, Ministry of Public Health of USSR, 1987, pp.27-29.

* cited by examiner

*Primary Examiner*—Michael G. Hartley
*Assistant Examiner*—J Rogers
(74) *Attorney, Agent, or Firm*—Brown & Michaels, PC (57) ABSTRACT

The inventive polyfunctional biocompatible hydrogel comprises 1.3–15 mass % of acrylamide, 0.004–0.975 mass % of cross-linking agents—N,N'-methylen-bis-acrylamide, 0.004–5.1 mass % of N,N'-ethylen-bis-acrylamide, 0.002–0.45 mass % of poviargol and water up to 100 mass %. Said hydrogel is produced by sopolymerising acrylamide with the cross-linking agents in an aqueous medium in the presence of peroxide polymerisation initiator, the incubation of reaction mixture being carried out in two stages. The first stage is carried out at a temperature ranging from 20 to 90° C. during a time of 2 to 24 hours, the second stage being carried out at a temperature ranging from 107 to 130° C. during a time equal to or less than 2 hours.

18 Claims, 8 Drawing Sheets

POLYFUNCTIONAL BIOCOMPATIBLE HYDROGEL AND METHOD FOR THE PRODUCTION THEREOF

REFERENCE TO RELATED APPLICATIONS

This is the US national phase filing of International Application No. PCT/RU01/00392, filed Sep. 28, 2001 to which priority is claimed and which is hereby incorporated herein by reference.

BACKGROUND OF THE INVENTION

Medical practice is faced with the task to produce artificial materials for replacement of soft tissues—muscular and subcutaneous tissue. They must be rather inexpensive, easy-to-make, and posses all specific physical and chemical characteristics including appropriate density and chemical inertness, the ability to shrink or swell, and the ability to be placed into the body which requires biological inertness, and, in particular, lack of antigenic activity causing rejection or any other tissue response. Additionally, the material must have a form which is suitable for injection into muscular tissue with minimum injury to the patient. Hydrogels based on polyarcylamide can be used for such purposes.

FIELD OF THE INVENTION

The invention pertains to the field of biocompatible hydrogels suitable for medical applications. More particularly, the invention pertains to the formula and method of production of a biocompatible hydrogel, based on the cross-linked copolymer of acrylamide with cross-linking agents. This gel can be used for medical purposes, for example:
- at endoprosthesis replacement by way of purposeful hydrogel injection for the augmentation of facial soft-tissues, mastoplasty, phalloplasty, augmentation of gastrocnemius muscles, vocal cords and other tissues, the density of which corresponds to the density of the hydrogel;
- as a filling compound for the manufacturing of endoprosthesis, including mammary endoprosthesis;
- as a depot for drugs during long pharmacotherapy, for example, during treatment of tumors or abscesses;
- as a carrier for cultivation of human and animal cells with the subsequent implantation of the hydrogel, which contains the above-mentioned cells, into the bodies of mammals.

DESCRIPTION OF RELATED ART

There is data on a hydrogel based on a copolymer of acrylamide with methylene-bis-acrylamide as a cross-linking agent. It is described in patent GB No.2114578. It is meant for production of lenses and contains 11% by mass of a copolymer comprising 100 parts acrylamide to 2.26 part methylene-bis-acrylamide in a physiologic salt solution.

The method of production of that hydrogel, described in the same patent (GB No.2114578) consists of copolymerization of acrylamide and methylene-bis-acrylamide, dissolved in a physiologic salt solution in the presence of polymerization initiators, one of which is tetramethylethylenediamine (TMEDA), with subsequent washing of the hydrogel from unreacted monomers. The copolymerization reaction is carried out in one stage at room temperature.

However, the hydrogel obtained this way is not suitable for utilization in soft-tissue augmentation due to its high density. Besides, on account of the copolymerization being carried out in one stage, such gel contains a high concentration of free radicals and monomers which exert negative influence on the organism's tissue response.

There is also data on a biocompatible hydrogel, described in application EP No.742022. It contains from 3.5 to 9.0% by mass of a cross-linked acrylamide-methylene-bis-acrylamide copolymer in water.

This hydrogel is produced by a method described in the same application (EP No.742022). That method consists of copolymerization of acrylamide with methylene-bis-acrylamide in aqueous solution in the presence of peroxide polymerization initiators. The reaction mixture must be held for 20 minutes at room temperature for linking of the copolymer. The copolymerization process is carried out in one stage. A mixture of ammonium persulfate and TMEDA is used as the peroxide initiator of polymerization. Pyrogen-free water or sodium chloride solution is used as aqueous medium.

The hydrogel made by this process has an inadequate degree of cross linking, as a result of the low temperature conditions of the copolymerization process and the one-stage reaction. This leads to a quick intrusion of connective tissue into the implanted gel and its rapid shrinkage and resorption in vivo (A. B. Shekhter et al. "Injectable hydrophilic polyacrylamide gel Formacryl and tissue response to its implantation", in "Records of Plastic, Reconstructive and Aesthetic Surgery", 1997, No 2, p.19).

Moreover, the hydrogel from this process contains unreacted TMEDA, free $NH_2$ radicals, and acrylamide monomers in the amount of 1.0–1.2 µg/g (1.0–1.2 ppm). This can provoke an inflammatory response at an early stage of the hydrogel's injection into the body. (A. B. Shekhter et all "Injectable hydrophilic polyacrylamide gel Formacryl and tissue response to its implantation", in magazine "Records of Plastic, Reconstructive and Aesthetic Surgery", 1997, No 2, p.19).

There is also data on a biocompatible gel, described in patent RU 2127129. It contains from 1.0 to 8.0% by mass of a cross linked acrylamide-methylene-bis-acrylamide copolymer in water. The method of its production is also described in patent RU 2127129. It consists in copolymerization of acrylamide with methylene-bis-acrylamide in aqueous medium in the presence of a peroxide initiator. In this reference water with a pH of 9.0–9.5, exposed to electrolysis, is used as the aqueous medium. Linking of the copolymer is carried out in two stages: at a temperature of 20–90° C. for 2–24 hours and then at a temperature of 100–105° C. for 2–4 hours.

The hydrogel from this process contains no TMEDA, slightly more than 1% of free $NH_2$ radicals and 0.6–0.8 ppm acrylamide monomers. However, after implantation into patients, there was observed shrinkage of the material of from 12% to 20% from original mass, depending on its water content. This reduces the cosmetic effect of the operation, and sometimes necessitates an additional injection of the material. Besides, polyacrylamide hydrogels can, like agar, serve as a medium for the reproduction of bacteria and it may provoke an inflammatory process if microorganisms contaminate the implant.

SUMMARY OF THE INVENTION

The present invention is aimed at the reduction of the resorption and shrinkage rate of biocompatible hydrogels based on cross-linked polyacrylamides after implantation into a patient's body.

A second aim is to reduce the possibility of colonization and proliferation of microorganisms within the hydrogel, including microorganisms already present in the patient.

Another aim is to diminish the concentration of free radicals and monomers in the hydrogel thereby reducing the possibility of adverse tissue responses to the implant.

These goals are achieved by a polyfunctional biocompatible hydrogel which contains copolymers of cross-linked acrylamide with a cross-linking agent and water. According to the invention, one suitable hydrogel comprises a copolymer containing a mixture of N,N'-methylene-bis-acrylamide, N,N-ethylene-bis-acrylamide and poviargolum with the following ratio of the components in percent by mass percent:

Acrylamide—65.0–99.5,
N,N'-methylene-bis-acrylamide—0.2–6.5,
N,N'-ethylene-bis-acrylamide—0.2–34.0, and
Poviargolum—0.1–3.0.

As a cross-linking agent, the above-mentioned copolymer can also contain vinylpyrrolidone or ethylene-bis-(oxyethylenenitrilo)-tetraacetic acid or a mixture thereof with the following ratio of the components in percent by mass percent:

Acrylamide—65.0–99.4,
N,N'-methylene-bis-acrylamide—0.2–6.5,
N,N'-ethylene-bis-acrylamide—0.2–34.0,
Poviargolum—0.1–3.0, and
Vinylpyrrolidone or ethylene-bis-(oxyethylenenitrilo)-tetraacetic acid, or a mixture thereof—0.1–2.5.

Wherein the above-mentioned biocompatible hydrogel: contains twice-distilled pyrogen-free water, has a pH of 3.5–7.5, and the cross-linked copolymer constitutes from 2.0 to 15.0% of the total mass of the hydrogel.

Another suitable biocompatible hydrogel according to this invention contains the following ratio of the components by mass percent:

Acrylamide—1.3–15,
N,N'-methylene-bis-acrylamide 0.004–0.975,
N,N'-ethylene-bis-acrylamide 0.004–5.1,
Poviargolum—0.002–0.45, and
Water—up to 98.69.

The biocompatible hydrogel can alternatively contain the following ratio of the components in mass percent:

Acrylamide—1.3–15,
N,N'-methylene-bis-acrylamide 0.004–0.975,
N,N'-ethylene-bis-acrylamide 0.004–5.1,
Poviargolum—0.002–0.45,
Vinylpyrrolidone or ethylene-bis-(oxyethylenenitrilo)-tetraacetic acid, or a mixture thereof—0.002–0.375,
Water—up to 98.688.

The challenges identified above are also solved by the proposed method of production of the polyfunctional biocompatible hydrogel. The copolymerization of acrylamide with the cross-linking agent(s) is performed in an aqueous medium in the presence of a peroxide polymerization initiator and incubation of the reaction mixture is done in two stages. The first stage is conducted at the temperature of 20–90° C. for 2–24 hours. In accordance with the invention, the cross-linking agent may be a mixture of N,N'-methylene-bis-acrylamide, N,N'-ethylene-bis-acrylamide and poviargolum with the following ratio of the components in mass percent.

Acrylamide—1.3–15,
N,N'-methylene-bis-acrylamide 0.004–0.975,
N,N'-ethylene-bis-acrylamide 0.004–5.1,
Poviargolum—0.002–0.45,
Water—up to 98.69, The second stage of the reaction mixture's incubation is conducted at a temperature of 107–130° C. for not more than 2 hours.

The method can be used even when the cross-linking agent is a mixture of N,N'-methylene-bis-acrylamide, N,N'-ethylene-bis-acrylamide, poviargolum, vinylpyrrolidone and/or ethylene-bis-(oxyethylenenitrilo)-tetraacetic acid with the following ratio of the components in mass percent:

Acrylamide—1.3–15,
N,N'-methylene-bis-acrylamide 0.004–0.975,
N,N'-ethylene-bis-acrylamide 0.004–5.1,
Poviargolum—0.002–0.45,
Vinylpyrrolidone or ethylene-bis-(oxyethylenenitrilo)-tetraacetic acid, or a mixture thereof—0.002–0.375,
Water—up to 98.688.

After the first stage of the incubation, the hydrogel is washed in hot water at 70–110° C. for at least 3 hours. The mass ratio of the hydrogel and water may be from about 1:8 to about 1:10.

The initiator of polymerization may be hydrogen peroxide and/or ammonium persulfate in the amount not more than 0.33 mass percent of the total of the original components.

Twice-distilled pyrogen-free water may form the aqueous medium.

It is known that hydrogels formed from a copolymer of acrylamide and cross-linking agents create a three-dimensional network of cross-linked copolymer of acrylamide with cross-linking agents. The voids present in such a three-dimensional network are filled with the aqueous medium in which polymerization occurred. Inevitably, this aqueous component contains a certain amount of initiator. Additionally, some amount of the initiator is incorporated directly into the copolymer's structure (see Savitskaya M. N., Kholodova Y. D. "Polyacrylamide", Publishing House "Tekhnika", 1969, p.103) or because it was rinsed out of the hydrogel during its washing.

The biological activity characteristics of such hydrogels depend largely on the structure of the cellular polymer, which in turn depends on the conditions of its synthesis, i.e. the quantitative and qualitative ratio of original reagents, including cross-linking agents and initiators of polymerization, which by means of covalent and hydrogen bonds get built into the copolymer's structure (by groups NH, CH, COOH, $NH_2$, $CH_2$), as well as the temperature of polymerization.

The main advantages of the present invention lie in the inclusion of N,N'-ethylene-bis-acrylamide and poviargolum as cross-linking agents into a hydrogel, based on an acrylamide and N,N'-methylene-bis-acrylamide copolymer, and in selection of conditions for copolymerization that mimimize the concentration of unreacted amides, free $NH_2$ radicals, and residual double bonds. The invention also makes possible an increase in the extent of cross-linking. Effectively increasing the formation of the cross-linking functional groups including:

(HC—NH—CH), (—CO—NH—CR—O—R), (—CO—NH—NH—CO—), (H—COR—NH—CR—O—R), (—CONH—R—NH—CO), where R=$CH_3$, $CH_2$, $NH_2$, $C_2H_5$, and increasing the number of cross-linking (N—N) connections.

These features reduce the tissue response of the patient upon implantation of the hydrogel, provide for high stability during implantation by reducing the rate of resorption and shrinkage, and reduce the possibility of colonization and proliferation of microorganisms within the hydrogel, including those from the recipient's body.

BRIEF DESCRIPTION OF THE DRAWINGS

Both infra-red spectra are exectured in the area of 4000–500 cm-1 (axis "x" represents the length of the light wave (cm-1); axis "y"—the degree of light absorption T (in %);

Both chromatograms are derived from high performance liquid chromatography (HPLC) with ultra-violet detection at a wavelength of 240 nm where peak 1 corresponds to the retention time of the solvent (acetonitrile) on the column, peak 2 corresponds to unreacted monomers in the hydrogel's extract. A unit (1 cm) of the height of peak 2 at the chromatogram corresponds to 0.057 ug of monomers, per1 g of polymer (0.057 ppm).

FIGS. 4b 4a represents a photomicrograph at 400×magnification of a histological section from a dog tissue biopsy, which was taken 9 months after subcutaneous injection of the hydrogel "Formacryl" (sample dyed with hematoxylin-eosin);

DETAILED DESCRIPTION OF THE INVENTION

In order to produce the biocompatible hydrogel of the present invention the following reagents were used:

Acrylamide: $C_3H_5NO$, molecular weight—71.08, white crystalline powder without any smell; melting temperature 84.5° C.; made by Sigma (Catalogue <<Reagents for Biochemistry and Research in the Area of Natural Sciences>> SIGMA, 1999, p. 47, catalogue No.A8887);

N,N'-methylene-bis-acrylamide: $C_7H_{10}N_2O_2$, molecular weight—154.16, white crystalline powder without any smell; melting temperature 85° C., made by Sigma (Catalogue <<Reagents for Biochemistry and Research in the Area of Natural Sciences>> SIGMA, 1999, p. 696, catalogue No.M7256);

N,N'-ethylene-bis-acrylamide: $C_8H_{12}N_2O_2$, molecular weight—168.2, made by Sigma (Catalogue <<Reagents for Biochemistry and Research in the Area of Natural Sciences>> SIGMA, 1999, p. 428, catalogue No.E2763);

Poviargolum—argentiferous detergent, powder, No.97/167/7 from Institute of High-Molecular Compounds of Russian Academy of Sciences (Russia), F. G.: 11.2 (Register of Drugs, Used in Russia—Aptekar, 2001, p.1067), which is a superfine metal silver, stabilized by poly-N-vinylpyrrolidone-2-ethylenebis(oxyethylenenitrilo)tetraacetic acid (see WWW:http://home.comset-.net/poviarg/; RU 2088234, published on Aug. 27, 1997);

Ethylene-bis(oxyethylenenitrilo)tetraacetic acid, molecular weight 380.35, melting temperature 249° C., made by Aldrich (Catalog handbook of Fine Chemicals Aldrich, 1994–1995, p.664, catalogue No.23,453-2);

1-vinyl-2-pyrrolidone: C6H9NO, molecular weight 111.4; melting temperature 93° C.; white powder; made by Fluka (Catalogue Fluka Chemika-Biochemika, Switzerland, sFr, 1993/94, p.1384, catalogue No.95060);

Ammonium persulfate: $(NH4)2\,S2O8$—molecular weight 228.19; colourless flat crystals; decomposition temperature 120° C.; made by Sigma (Catalogue <<Reagents for Biochemistry and Reasearch in the Area of Natural Sciences>> SIGMA, 1999, p.117);

Hydrogen peroxide: $H_2O_2$—molecular weight 34.0; colourless fluid, density at 0° C.–1,465; melting temperature –0.89° C.; made by Sigma (Catalogue <<Reagents for Biochemistry and Research in the Area of Natural Sciences>> SIGMA, 1999, p. 556, catalogue No.H6520);

All above-mentioned monomers shall be suitable for biological purposes and shall not require additional cleaning.

Water shall be twice-distilled and pyrogen-free (pH=5.6).

The method must be conducted the following way:

In order to prepare the compound we take twice-distilled pyrogen-free water with pH of 5.6.

We prepare an aqueous solution of acrylamide and cross-linking agents, for example, the mixture of N,N'-methylene-bis-acrylamide, N,N'-ethylene-bis-acrylamide and poviargolum (taken in the given mass ratio within the following limits: 65.0–99.5:0.2–6.5:0.2–34.0:0.1–3.0 respectively), or a mixture of N,N'-methylene-bis-acrylamide, N,N'-ethylene-bis-acrylamide, poviargolum, vinylpyrrolidone or ethylenebis(oxyethylenenitrilo) tetraacetic acid, or combinations of the latter two (taken in the given mass ratio within the following limits: 65.0–99.4:0.2–6.5:0.2–34.0:0.1–3.0: 0.1–2.5 respectively), such that the total mass of monomers in the solution makes up 2.0–15.0%. (By modifying the amount of the monomers in the solution, we get the hydrogel of different density and flexibility).

Into this solution we introduce the polymerization initiators hydrogen peroxide in the amount of 0.1–0.3 mass % or ammonium persulfate in the amount of 0.0006–0.03 mass %, or a mixture of these two in any correlation and amount, not exceeding the sum of their individual maximum vales. By modifying the amount of hydrogen peroxide and ammonium sulfate, we receive a substance with a pH within the desired range of 3.5–7.5.

The above mixture is filtered through a bactericidal polymer filter, (for example Sigma (USA) part number F8273 with a pore size of 0.45 μm) and then incubated at a temperature of 20–90° C. for 2–24 hours. After incubation, the product, which looks like a gel, is washed with hot water. For that purpose the gel is placed into a reservoir with water of 90–100° C. with the ratio of the gel and water of from 1:8 to 1:10 for 4–6 hours. Then the second stage of the incubation is carried out at the temperature of 107–130° C. for 1.0–1.5 hour.

The gel thus produced is packed in the necessary amount into bottles or syringes and sterilized by autoclaving (at the temperature of 120° C. and a pressure of 1.2 atm.) for 20 minutes.

We carried out physical and chemical, medical and toxicological examinations of the gel samples, including those received in the below-mentioned Examples 1–5, in accordance with ISO 10993 "Evaluation of Biological Effect of Medical Devices", "Methodical Directions on Sanitary and Hygienic Evaluation of Rubber and Latex Devices, Meant for Medical Purposes" (Ministry of Public Health of USSR, Moscow, 1988) and methodological recommendations in "Admissible amount of migration of chemical agents, that are exuded from polymer and other materials in contact with food hydrogels and methods of their determination" Sanitary Rules and Standards 42-122-42-40-86.

The determination of the concentrations of the monomers for acrylamide, N,N'-methylene-bis-acrylamide, N,N'-ethylene-bis-acrylamide and ethylenebis(oxyethylenenitrilo) tetraacetic acid were carried out in accordance with the methods, described in the work of V. V. Kuznetsov et al. <<Determination of Acrylamide in Polyacrylamide gels"// The 52-nd Pittsburgh Conference on Analytical Chemistry and Applied Spectroscopy.—New Orleans, La., 2001, Abstract Book, N.1648.

These researches revealed that the hydrogel of the present invention has the following physical and chemical characteristics:

Appearance—gel

Colour—from colourless to semitransparent dark brown, opalescent;

Refractive index—1.328–1.360;

Density—1.0–1.2 g/cm3;

pH—3.5–7.5;

Monomer content—up to 0.4 ppm;

Bromation rate—not more than 1.0 (mg of bromine for 1 L of gel).

Sanitary and chemical examination revealed the following:

Migration of metals—Cu, Fe, Ni, Zn, Al, Ti, Ag from the hydrogel into the aqueous extract, determined by an atomic absorptive method, was found to be below the limits of detection for the instrument (0.02; 0.05; 0.05; 0.02; 0.005; and 0.04 mg/l respectively), which is a figure considerably lower than those allowable for drinking water;

Migration of sodium constituted not more than 0.12 mg/l while the admissible level is 200 mg/l for drinkable water;

Toxicological examination showed that aqueous extracts from the hydrogel did not reveal a hemolytic effect in "in vitro" experiments with isolated erythrocytes of rabbits. The hemolysis rate was found to be 0.04% while the maximum admissible rate is 2%.

Zone of growth inhibition of Staphylococcus aureus by the agar disk diffusion method, determined as described in the guide "Method for Determination of Microorganisms' Antibiotic Perceptibility by Disk Diffusion Technique", Moscow, Ministry of Public Health, 1984, was 1.5–3 mm, depending on the density of the sample (polyacrylamide content).

In an acute toxicity study in white mice with parenteral introduction of hydrogel samples in the amount of 50.0 ml per 1 kg of animal weight, there were neither loss of animals nor clinical signs of intoxication: general condition of the mice under the experiment, their behaviour, eating, state of hair had no difference from those in an untreated control group.

Autopsy of the mice from this experiment showed that the tissues at the site of hydrogel injection, regional lymph nodes, internals (liver, kidneys, spleen) were within the boundaries of physiologic norms and control.

We have not found any statistically relevant differences in dynamics of body weight, clinical and biochemical blood indices, or coefficients of internals of the animals under experiment in comparison with the control group with the subcutaneous implantation of the gel for 2.5 months.

We have not found any sensitizing effect of the hydrogel in an immunologic diagnostic reaction of mast cells' degranulation reaction.

Microkernel test on bone marrow showed no mutagenic effect of the hydrogel. Histological examination of area where the hydrogel was implanted, and internals (liver, kidneys, spleen, testicles) showed a slight tissue response to the hydrogel only in the first days after the implantation. There were no dystrophic and necrotic changes in the organs.

Below there are the specific examples of how the present biocompatible hydrogel is produced and used for soft-tissue augmentation.

EXAMPLE 1

In order to produce the hydrogel we took 384 ml of twice-distilled pyrogen-free water with pH 5.6 and dissolved in it 13 g of acrylamide, 5.5 g of N,N'-methylene-bis-acrylamide, 2.3 g of N,N'-ethylene-bis-acrylamide and 0.2 g of poviargolum, suitable for biological purposes. This solution was combined with 0.04 g of ammonium persulfate and 2 ml of 30% hydrogen peroxide. The solution was filtered through a bactericidal polymeric filter with pores of 0.45 μm made by Sigma (USA), and put into a reservoir, which was incubated at 30° C. for 22 hours. Then the product in the form of a gel was washed in hot water with a 10:1 ratio of water to gel at 90° C. for 4 hours and again incubated for 1 hour at a temperature of 125° C.

The hydrogel thus produced was sterilized by autoclaving (at the temperature of 120° C. and pressure of 1.2 atm.) for 20 minutes.

The gel produced contains 96% water 4% of copolymer by mass, in which the copolymer contains acrylamide 81.25%, N,N'-methylene-bis-acrylamide 3.125%, N,N'-ethylene-bis-acrylamide 14.375% and poviargolum 1.25% by mass. It has a pH of 5.4.

We examined the following characteristics of the hydrogel:

Refraction index (by the methods, described in "Practical Work on Physical Chemistry", Moscow, 1974, pp 86–97);— pH (by the methods, described in the book "Methodical Directions on Sanitary and Hygienic Evaluation of Rubber and Latex Devices, Meant for Medical Purposes", Moscow, 1988, pp 18–19);—bromation level (by the methods, described in "Collected Guide Materials On Toxicological Examination of Polymeric Materials and Devices for Medical Purposes, Made on Their Bases", Moscow, Ministry of Public Health of USSR, 1987, pp.27–29);

monomers' content—by the methods, we developed for determination of monomers' content in hydrogenous polymers: V. V. Kuznetsov et al. <<Determination of Acrylamide in Polyacrylamide Gels"// The 52-nd Pittsburgh Conference on Analytical Chemistry and Applied Spectroscopy.—New Orleans, La., 2001, Abstract Book, No.1648.

The sample of the gel had the following physical and chemical characteristics:

Appearance—colourless, semitransparent, opalescent gel;
Refraction index—1.348;
pH—5.4;
Density—1.0 g/cm3;
Monomers' content—0.1 ppm;
Bromation level—0.1(mg of bromine per 1 of gel).

Figure 1A:
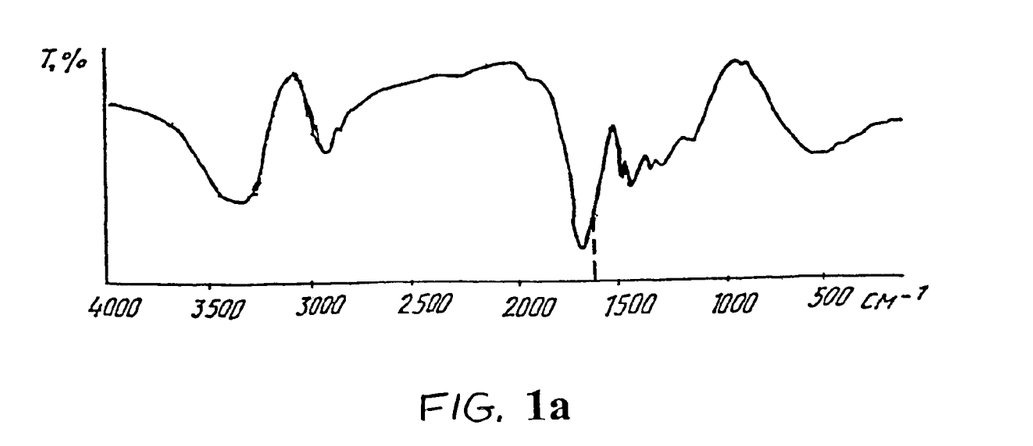
FIG. 1a represents infra-red absorption spectrum for a hydrogel of the invention
Figure 2A:
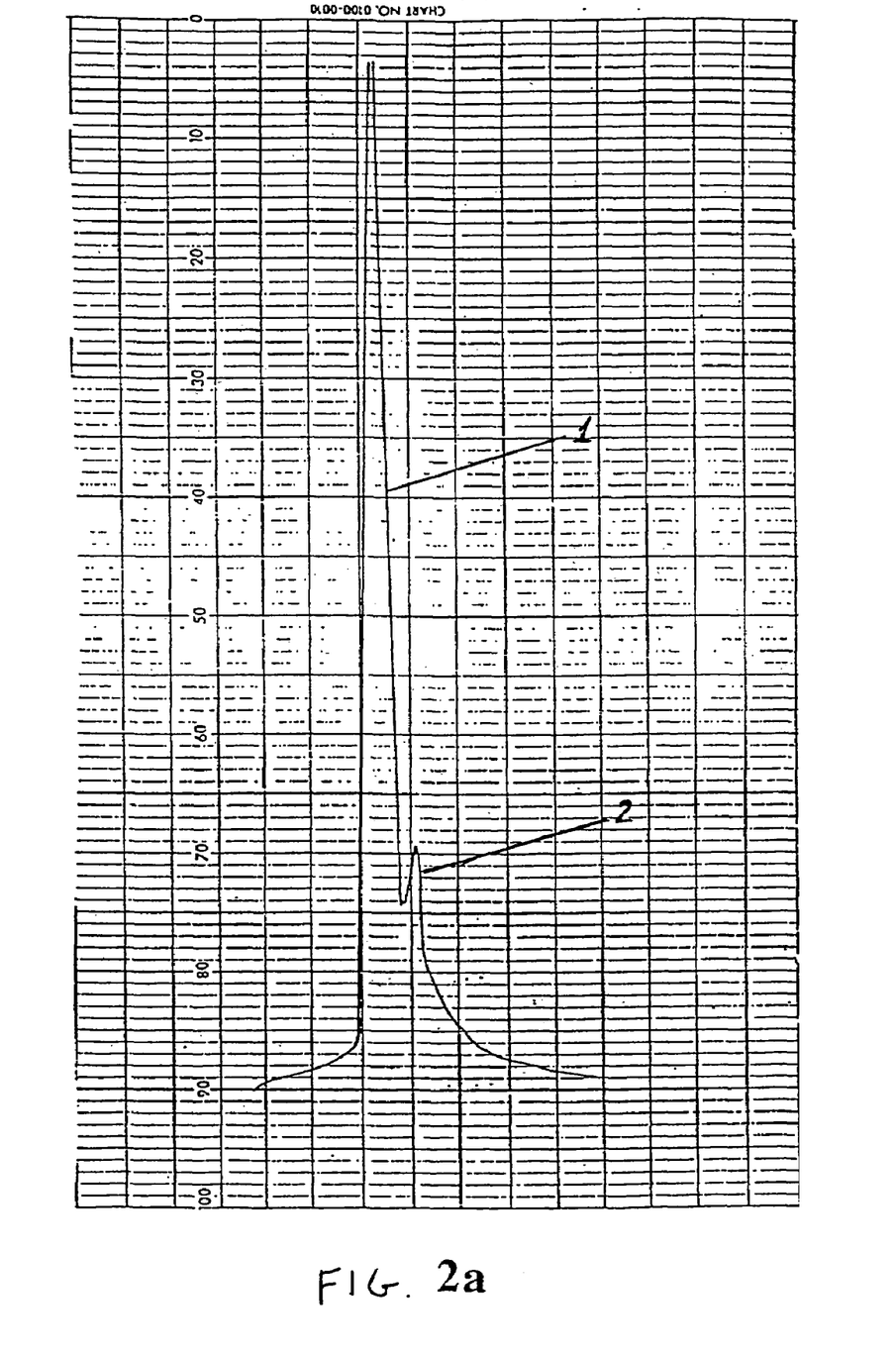
FIG. 2a represents chromatogram of the present invention's hydrogel's extract.

We obtained the infra-red absorption spectrum and HPLC chromatograms of the hydrogel's extract, represented in FIG. 1a and FIG. 2a respectively.

Figure 1B:
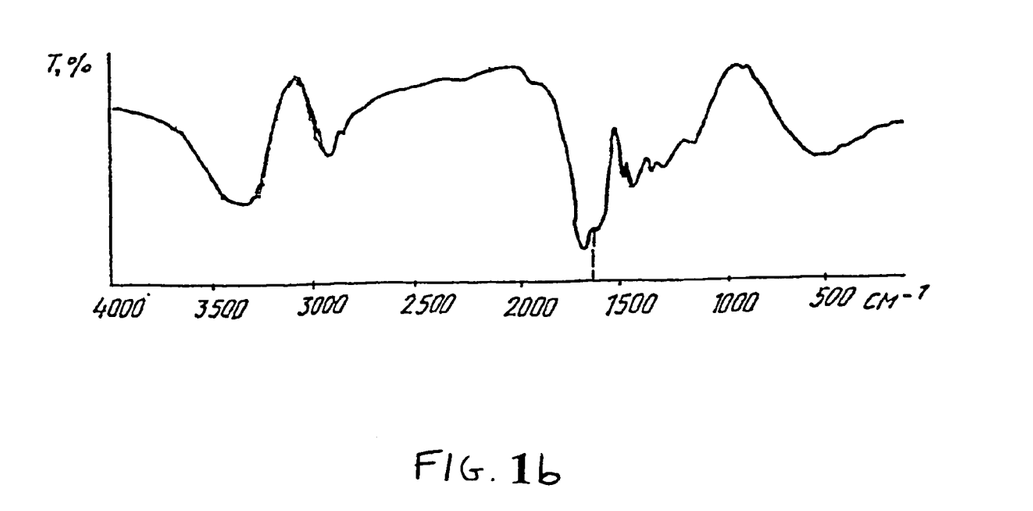
FIG. 1b represents infra-red absorption spectrum for the hydrogel-prototype, manufactured in Russia under patent RU No.2127129 under trademark "Formacryl"
Figure 2B:
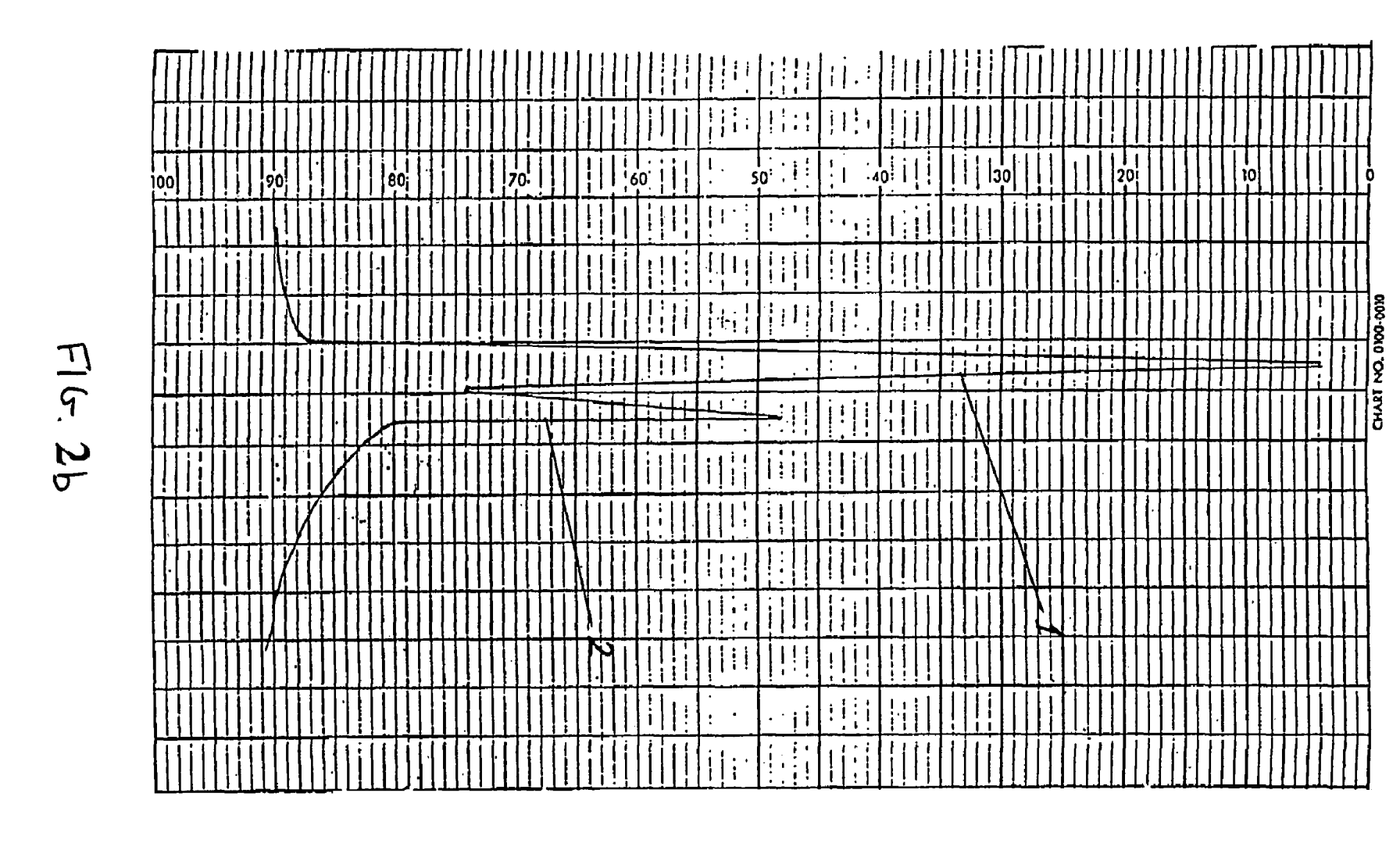
FIG. 2b represents chromatogram of the extract of hydrogel "Formacryl".

For comparison FIG. 1b and FIG. 2b represent the infrared spectrum and HPLC chromatogram of an extract of the well-known hydrogel-prototype, manufactured in Russia under patent RU No.2127129 under the trademark "Formacryl", which contains 96% of the water phase and 4% of the copolymer, respectively with the copolymer composed of 96% acrylamide and 4% of N,N'-methylene-bis-acrylamide by mass. It has pH=5.4, bromation level 0.27 (mg of bromine for 11), and was produced by incubation of the initial mixture in the presence of hydrogen peroxide and ammonium persulfate in the total amount of 0.3% at 60° C. for 12 hours and then at the temperature of 100° C. for 2 more hours.

As is evident from the spectrum in FIG. 1a, there is no absorption in the region of 1620 cm-1, characteristic of the bond vibrations of $NH_2$ radicals, nor in the regions of 3200 cm-1 and 3600 cm-1 resulting from the N—H bond stretching of these radicals. This is indicative of the fact that free $NH_2$ radicals constitute not more than 1% of the total number of functional groups in the polymer's structure.

As is evident from the spectrum of FIG. 1b, there is a zone of absorption at 1620 cm-1, which is indicative of the fact that there is more than 1% of $NH_2$ radicals.

As indicated the chromatogram of FIG. 2a, peak 2, which corresponds to the total amount of monomers of acrylamide, N,N'-methylene-bis-acrylamide, and N,N'-ethylene-bis-acrylamide, does not exceed a height of 5.1 cm, which corresponds to a monomer content of 0.29 ppm.

As is obvious from the chromatogram, of FIG. 2b, the content of monomers of acrylamide and N,N'-methylene-bis-acrylamide in Formacryl constitutes 0.6 ppm, since the height of the peak is 10.7 cm.

We also studied the bacteriostatic features of the sample of hydrogel. We used disk-diffusion methods using a Staphylococcus aureus strain.

It was established that the zone without cell growth around the sample constituted 1.5±0.1 mm with the hydrogel of the present invention, while there was no zone without growth around the control sample of "Formacryl" having the same density. Moreover, we observed the growth of bacteria directly under the dark of "Formacryl".

We examined the shrinkage rate of the hydrogel of the present invention in comparison with the similar characteristics of "Formacryl". For that we made a subcutaneous implantation of 30 ml samples of the invention's hydrogel and the hydrogel "Formacryl", in dogs, with the subsequent removal of the samples and measurement of the dry residue and water phase of the hydrogel one, three and six months after the implantation. It was established that even when the hydrogel of the invention stayed in the animal for 6 months, the loss of water phase constituted not more than 5% of its original content in the implant, while the loss of the water phase in the implanted sample of hydrogel "Formacryl" constituted about 10% under similar conditions. The amount of dry residue in both cases was practically unchanged.

We examined the tissue response to the implantation of the hydrogel of the present invention in experimental-morphological and clinical-morphological studies.

The study was carried out on 160 male rats, weighing 200 g, and 10 dogs.

The rats received a 1 ml injection of the hydrogel subcutaneously.

The terms of the morphological study constituted 3, 7, 14, 30, 60 and 90 days.

Long-term implantation (6–12 months) was examined in dogs injected with 15 ml of the hydrogel subcutaneously.

In the clinic, the morphological study of tissues after the implantation of the same hydrogel to 5 patients was carried out: 1 month after the implantation under the skin in the facial area, 1.5 and 3.5 months after intramuscular implantation into the crus, and 6 and 12 months after the implantation, meant for increasing mammoplasty by way of filling the fibrous capsule's cavity with the gel after silicon prostheses were taken out.

In order to carry out the histological study, the tissue blocks were fixed in 96° ethyl alcohol and neutral formalin and covered by paraffin. The cuts were coloured by hematoxylin-eosin, picrofuxin by Van-Gizon, silvering by Gommori to study the fibrous components, blue toluidine for soar glycosaminoglycans, studied PAS-reaction for glycogen and glycoprotein as well as Brachet reaction for RNA.

Figure 3A:
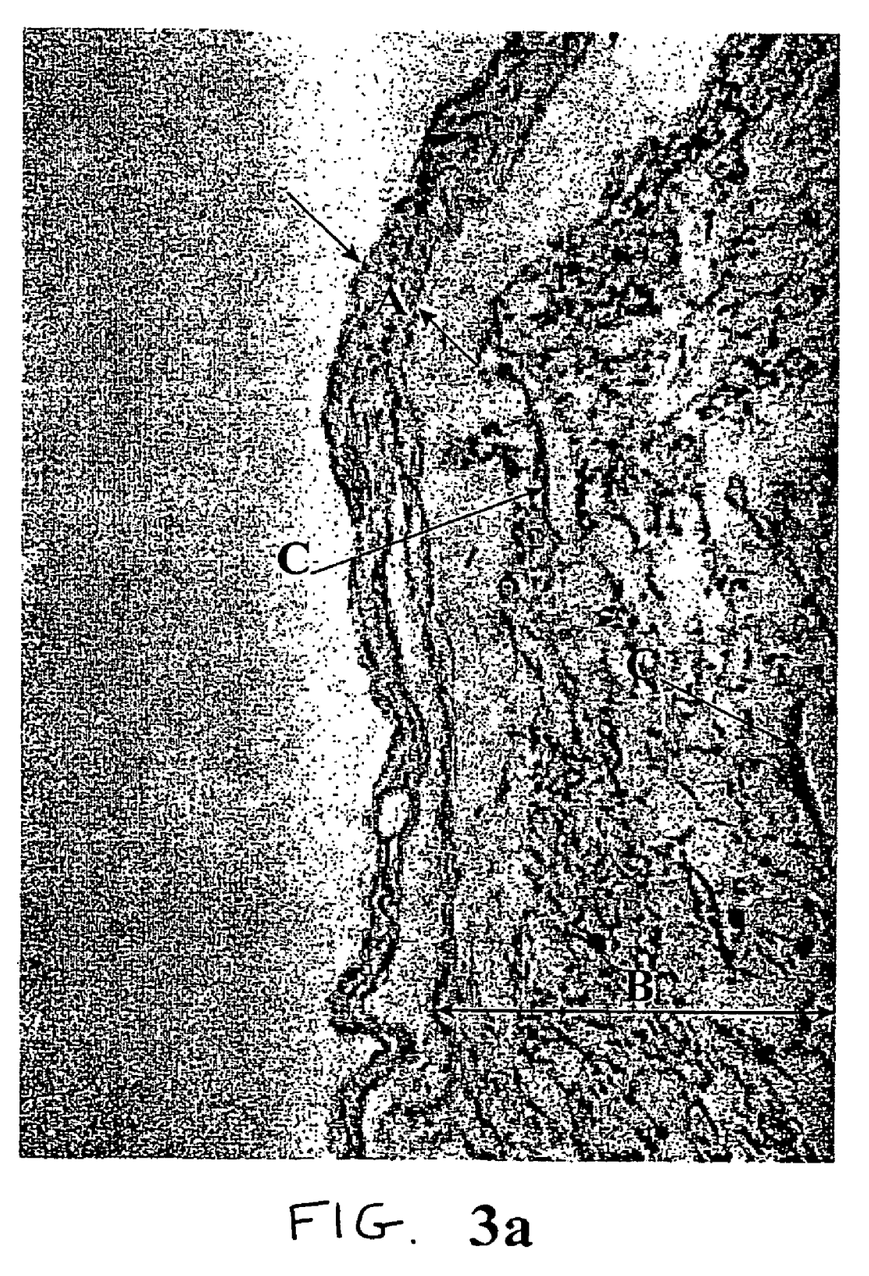
FIG. 3a represents a photomicrograph at 200×magnification of a histological section from a rat tissue biopsy, which was taken 30 days after subcutaneous injection of the hydrogel of the invention (sample dyed with hematoxylin-eosin)
Figure 4A:
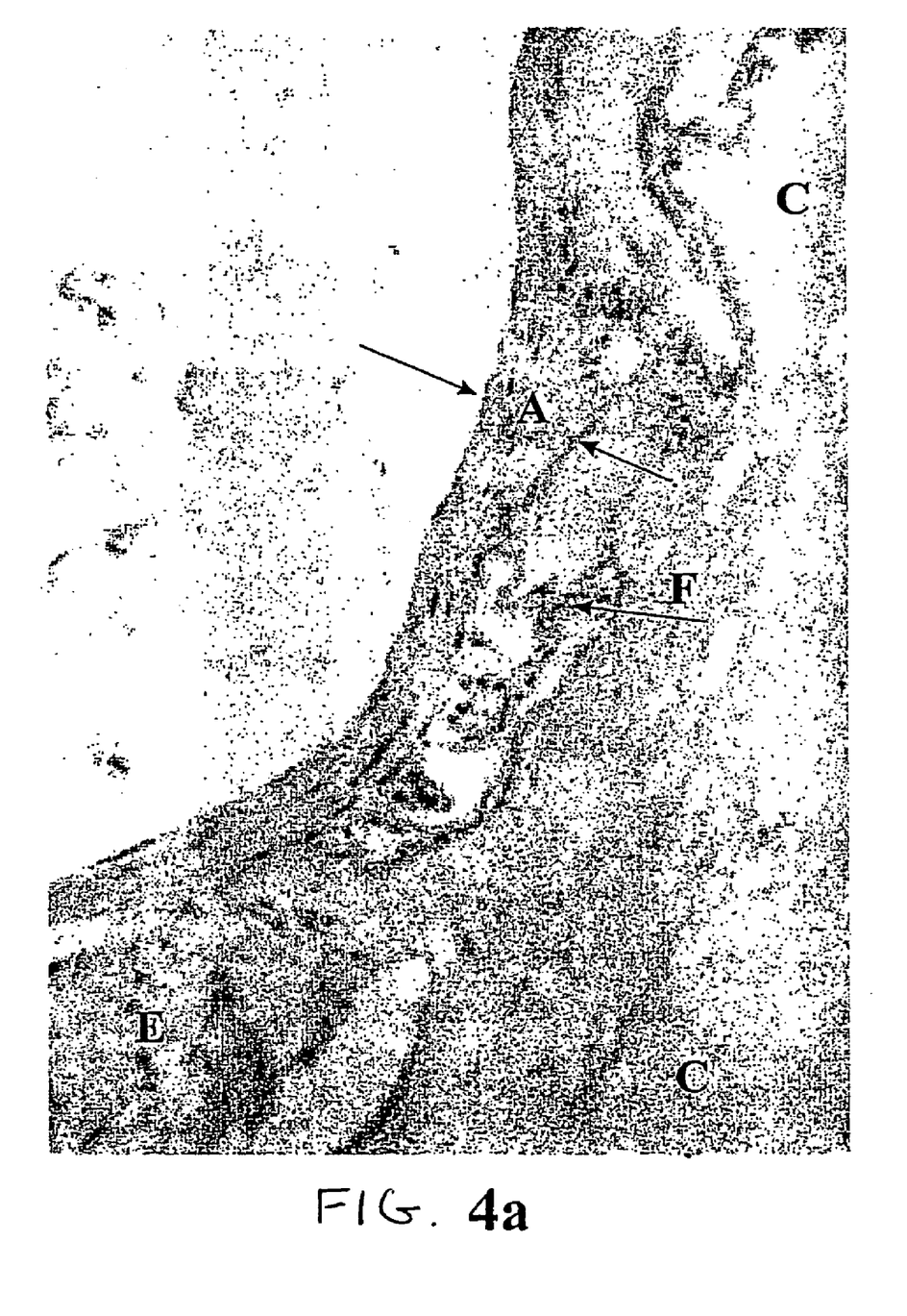
FIG. 4a represents a photomicrograph at 400×magnification of a histological section from a dog tissue biopsy, which was taken 9 months after subcutaneous injection of the hydrogel of the invention (sample dyed with hematoxylin-eosin)
Figure 5:
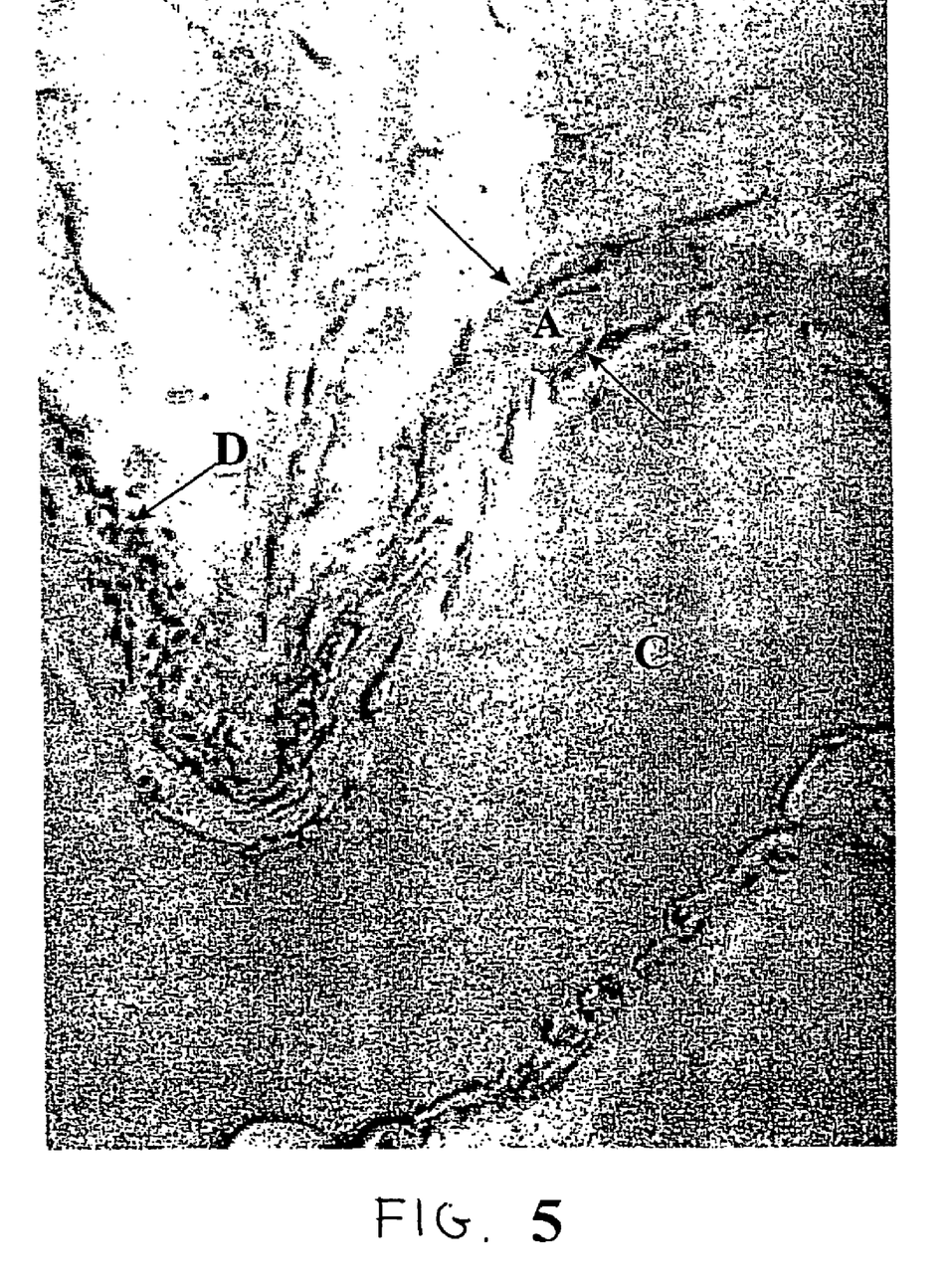
FIG. 5a represents a photomicrograph at 400×magnification of a histological section from a human tissue biopsy which was taken 12 months after sub-tonsils implantation of the hydrogel of the invention intended for mammoplasty (sample dyed with hematoxylin-eosin), Where A—a connective capsule,
B—zone behind the capsule,
C—a fragment of the hydrogel,
D—macrophages on the surface of capsule A from the side of the implant,
E—zone of the hydrogel's lysis,
F—cords of the connective tissue.

Some results of the histological studies are represented on FIGS. 3a, 4a, 5.

Morphologic study of the organism's tissue response to the implantation of the hydrogel, conducted on rats, shows a minimal response. In the early days (3–7 days after the implantation) the response is limited to a slight lympho-macrophage infiltration with single neutrophils and feeble tissue edema. This is indicative of a minimal inflammatory response. On the third day we observed the proliferation of fibroblasts in a narrow zone around the implant, and on the seventh day there had formed a very thin connective capsule, which consisted of fibroblasts and thin collagen fibers. Inside, the capsule was covered with a layer of macrophages, bordering the implant. In 14 days the capsule is more clearly defined, but it is still thin and friable. Inside the capsule, as well as between it and the cellular tissue (behind the capsule) we see small fragments of the hydrogel, surrounded by macrophages and single giant multinucleous cells. 30 days after the implantation the capsule A (FIG. 3a) remains very thin. It consists of the mature connective tissue, the amount of fibroblasts in which is diminishing, and in the remaining cells the content of RNA is diminishing. Behind the capsule, in zone B there are still fragments C of the hydrogel, which are resorbed by macrophages. The inner surface of the capsule is partially covered by macrophages. In the future terms (60 and 90 days) the structure of the capsule remains unchanged, inside the gel there come some cords of fibroblasts from the capsule.

Figure 3B:
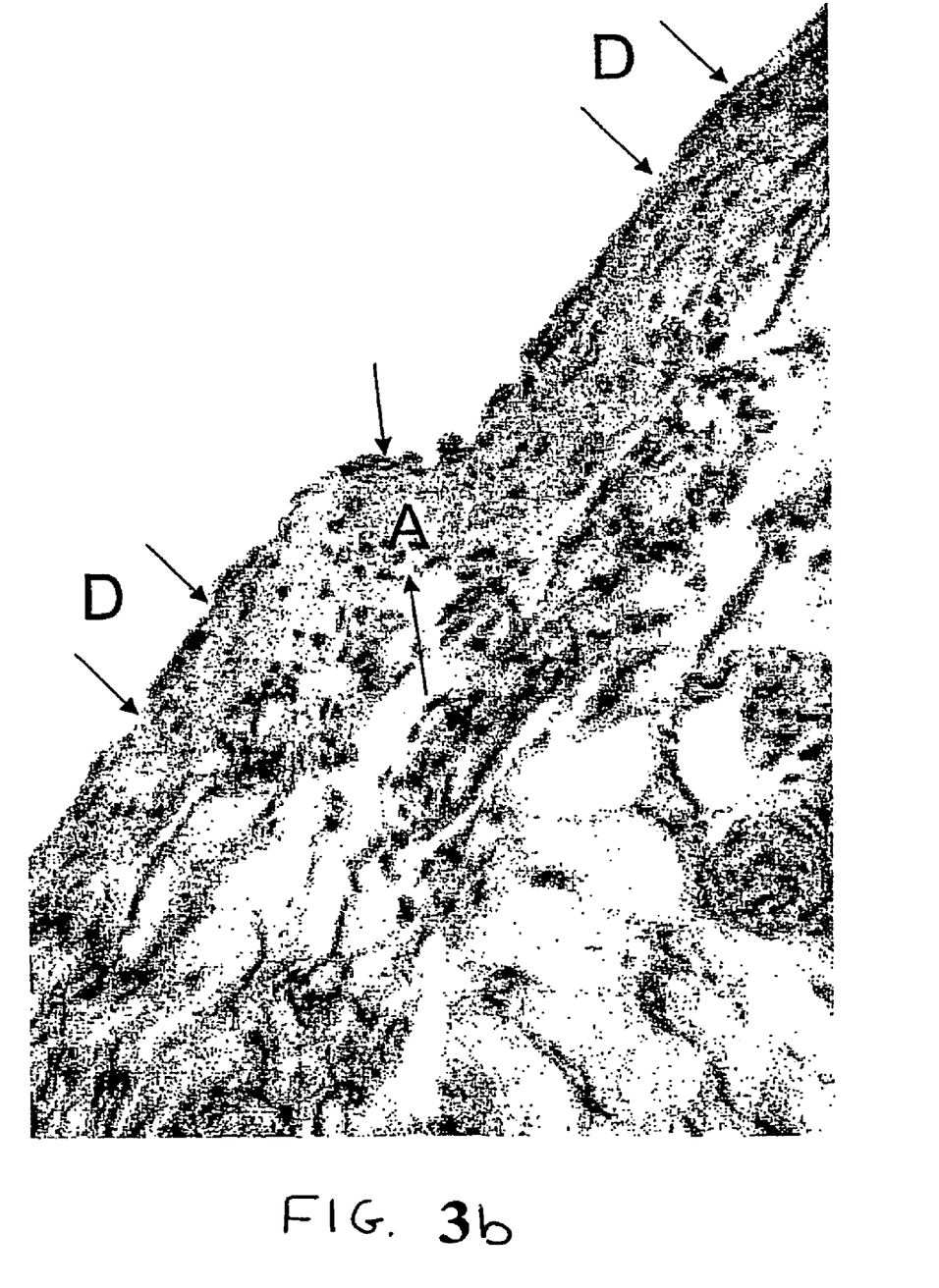
FIG. 3b represents a photomicrography at 200×magnification of a histological section from a rat tissue biopsy, which was taken 30 days after subcutaneous injection of the hydrogel "Formacryl" (sample dyed with hematoxylin-eosin)

For comparison, FIG. 3b represents the photo of the histological cut of the rat tissue biopsy, taken 30 days after the subcutaneous injection of the hydrogel-prototype ("Formacryl"). As is seen from the photo on FIG. 3b, the connective capsule A around the implant is much thicker than at the implantation of the hydrogel of the present invention. Inside the capsule, the inner surface and in the capsuled zone there is an increased number of macrophages D, giant multinucleous cells and neutrophils, which is indicative of a slight inflammatory process.

The tissue response in the later terms (6, 9 and 12 months) was studied on a subcutaneous implantation of the hydrogel to dogs. As it is seen from FIG. 4a, 9 months after implantation the hydrogel C retains its homogeneous structure for the most part. Near a very thin and dense connective capsule A there is a narrow zone E of the hydrogel's enlightment (lysis), which is resorbed by macrophages and infiltrated by cords F of fibroblasts. There is no deep infiltration of cells into the hydrogel. This is indicative of its long-term stability. There are no lime deposits in the capsule or in the hydrogel. There are dystrophic changes of the cells in the tissue around the implant, which could be indicative of the toxicological influence of the hydrogel.

Figure 4B:
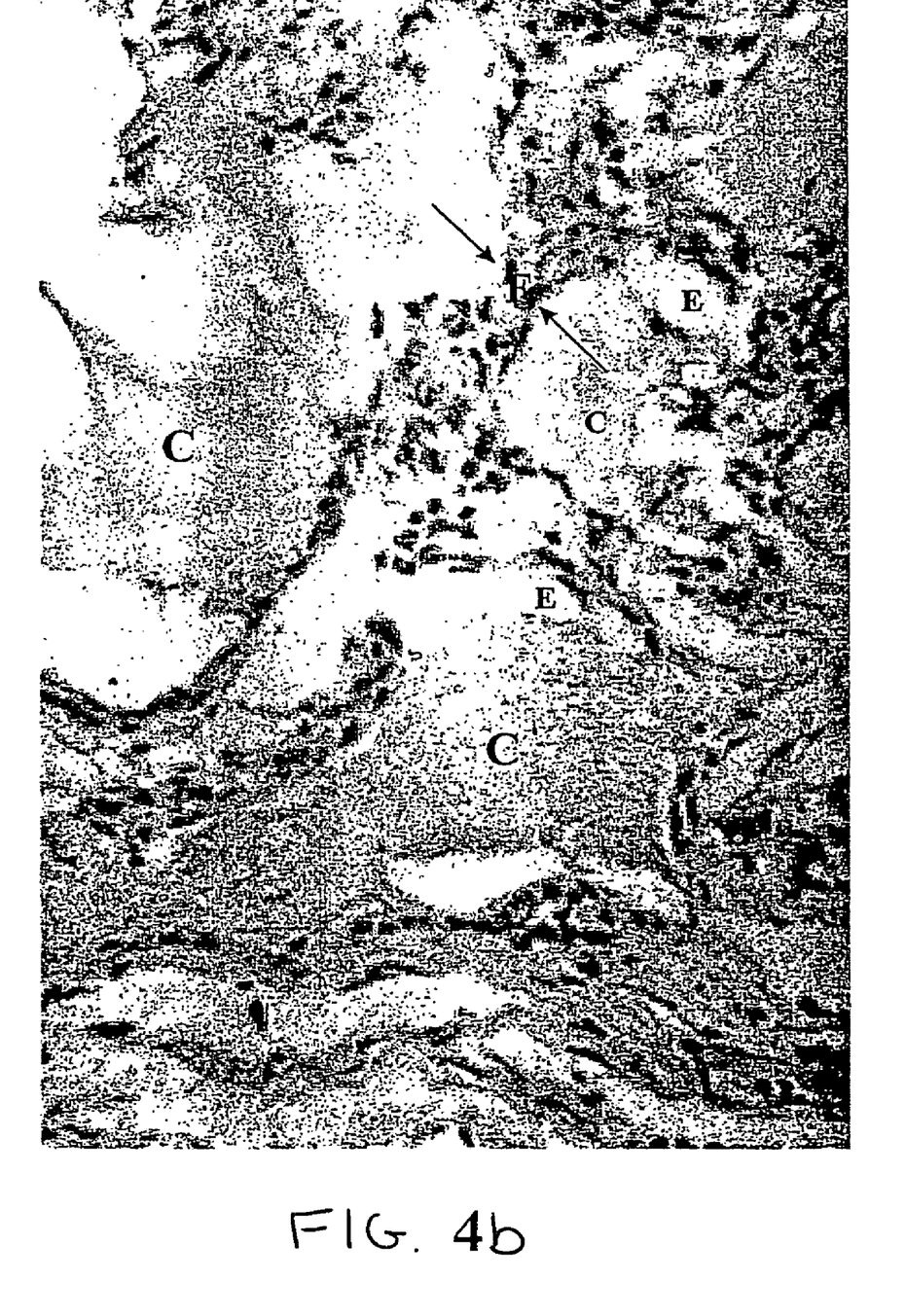

For comparison, FIG. 4b represents a photo of the histological cut of the dog's tissue, taken 9 months after the subcutaneous implantation of the sample (the same as for FIG. 3b) of the hydrogel-prototype Formacryl (colouring by hematoxylin-eosin, ×400).

As it is seen from the photo gel C is infiltrated with cords F of connective tissue, which contains fibroblasts, macrophages, leukocytes and single neutrophilic leukocytes. There is a partial lysis E of the gel and its resorption.

Clinical and morphological studies, conducted 1 month after the injection of 90 ml of the sample of the hydrogel of the present invention for dermotension of the skin and fat part of the face with the purpose of the subsequent cicatrices plasty, showed that on the border between the hydrogel and tissues there is forming a very thin and friable connective tissue, made of only several layers of collagen fibres and fibroblasts. The cellular lympho-macrophagal infiltration is minimal. In some zones outside the capsule there can be seen tissue vacuoles, remaining in place of resorbed gel. There is a slight macrophagal and gigantocytous response.

Similar results were obtained in two cases of study of contour plasty of crus' soft tissues by way of injection of the hydrogel of the present invention. 1.5 and 3.5 months after the implantation the gel remained homogeneous for the most part and was infiltrated by the connective tissue only around the capsule. FIG. 5 represents the results of the morphological study of biopsy, taken 12 months after the injection of the sample of 200 mL of the hydrogel in place of taken-out silicon prosthesis in the cavity of the remaining fibrous capsule.

As it can be seen on FIG. 5, the tissue response to the gel is slightly expressed. The "old" fibrous capsule is subject to a reverse development nearly everywhere. Implant C is surrounded by a thin connective capsule A without inner miofibroblastic layer, which is present in the capsules around silicon prostheses. In the "new" capsule there are not numerous macrophages D and lymphocytes without any inflammatory neutrophilic reaction. Vessels of the capsule are not numerous, and there are no dystrophic changes or deposits of calcium salts.

Near the capsule A there is a rather shallow infiltration of thin cords of connective tissues (fibroblasts, macrophages and therein immature collagen fibres) into the hydrogel. Some macrophages have a large foamy cytoplasm (active phagocytosis). Cords of the connective tissue divide the gel near the capsule into the fragments.

Thus, the result of the histological studies, received in a long dynamics on animals, as well as on bioptic clinical material, are indicative of the high biocompatibility of the hydrogel of the present invention.

In the early periods after injection of the samples of the present invention's hydrogel into the organism, we observed a very feeble and quickly disappearing inflammatory response, fibroblastic response was slow and feeble, the capsule was formed late and remained thin during the whole period of observation.

It is characteristic that there was no deep invasion of macrophages and microphages into the hydrogel. This confirms the stability of the hydrogel towards the resorption in the organism. The hydrogel does not diminish the functional activity of the cells and does not lead to their dystrophy, which is indicative of the absence of toxic substances migrating from the gel into the tissue. There is also no calcification of the hydrogel and surrounding tissues.

The hydrogel of the invention was injected to patient L-kaya, 55 years old, instead of the hydrogel which was used for initial mammoplasty 5 years earlier and which led to the inflammatory process in both mammary glands. In the postoperative period the patient was observed for 8 months with monthly examination. There was no recurrence of the inflammatory process. We received a positive result: mammary glands acquired the form and size corresponding to the patient's constitution, and elasticity, characteristic of the tissue of a healthy mammary gland.

EXAMPLE 2

In order to produce the hydrogel we took 870 ml of twice-distilled pyrogen-free water with pH 5.6 and dissolved in it 81.0 g of acrylamide, 11.5 g of N,N'-methylene-bis-acrylamide, 32.9 g of N,N'-ethylene-bis-acrylamide and 4.6 g of poviargolum. Then the solution was combined with 8 ml of hydrogen peroxide in order to initiate polymerization. The solution was filtered as described in Example 1, placed for incubation at 80° C. for 2 hours. Then the gel was washed in 10 liters of hot water at 80° C. for 5.5 hours and again incubated for 1. hours at 125° C.

The hydrogel thus formed was sterilized as described in Example 1.

The hydrogel had the following physical and chemical characteristics, which were determined in accordance with the methods, specified in Example 1:
  Appearance—semitransparent, light yellow gel;
  Refraction index—1.336;
  pH—4.0;
  Density—1.0 g/cm3;
  Content of monomers of acrylamide and bisacrylamide—up to 0.4 ppm; and
  Bromation level—0.9(mg of bromine for 1l);
  Bacteriostatic features
  Zone of bacterial growth inhibition—2.5 mm.

The hydrogel was used for gastronemius muscle plasty. The hydrogel in the amount of 50 ml was injected into the gastrocnemius muscle of patient I., 42 years old, in order to eliminate the defect of the trauma she had received.

In the postoperative period the patient was observed for 6 months. There were no inflammatory reactions or edema. The gel's migration was absent. The cosmetic effect was achieved.

EXAMPLE 3

In order to produce the hydrogel we took 972 ml of twice-distilled pyrogen-free water with pH 5.6 and dissolved in it 22.5 g of acrylamide, 0.375 g of N,N'-methylene-bis-acrylamide, 5 g of N,N'-ethylene-bis-acrylamide, 0.06 g of poviargolum and 0.065 g of ethylene-bis-(oxyethylenenitrilo)-tetraacetic acid. This solution was combined with 2.5 g of ammonium persulfate. The mixture was filtered as described in Example 1, and placed for incubation at 80° C. for 2 hours. Then the gel was washed in 8 liters of hot water at the temperature of 100° C. for 5.5 hours and again incubated for 1.5 hours at 125° C.

The hydrogel thus formed was sterilized as described in Example 1.

The hydrogel had the following physical and chemical characteristics, which were determined in accordance with the methods, specified in Example 1:

Appearance—colourless gel;
Refraction index—1.334;
pH—6.8;
Density—1.0 g/cm3;
Content of monomers of acrylamide—absent;
Content of the other monomers—0.02 ppm;
Bromation level—0.15(mg of bromine for 1l);
Bacteriostatic features
Zone of bacteria's growth suppression—1.5 mm We conducted a comparative study of the shrinkage rate of the samples of this hydrogel and its prototype "Formacryl", which contain the same amount of polyacrylamide: 2.8% by mass For this study, 30 ml samples of the hydrogel were injected subcutaneously in dogs and taken out 3 and 6 months after that.

The determination of dry residue and water phase in the taken-out implants showed that:

4 months after the implantation Formacryl lost 20% of water, and 6 months after the implantation it lost 30% of water;

4 months after the implantation the hydrogel of the present invention, which contained the mixture of N,N'-methylene-bis-acrylamide, N,N'-ethylene-bis-acrylamide and poviargolum as a cross-linking agent, lost 10% of water, and 6 months after the implantation it lost 15% of water;

4 months after the implantation the hydrogel of the present invention, which contained the compound of N,N'-methylene-bis-acrylamide, N,N'-ethylene-bis-acrylamide, poviargolum and ethylene-bis-(oxyethylenenitrilo)-tetraacetic acid, as a cross-linking agent, lost 5% of water, and 6 months after the implantation it lost 9% of water.

Thus, the introduction of ethylene-bis-(oxyethylenenitrilo)-tetraacetic acid (or vinylpyrrolydone or the mixture of these two substances) provides for the diminishing of the implant's shrinkage rate, which is characteristic of the hydrogels with a low dry residue content.

The hydrogel with a small dry residue content, up to 3%, can be easily injected through thin needles and can be used for the augmentation of facial soft tissues. However, without the introduction of ethylene-bis-(oxyethylenenitrilo)-tetraacetic acid into the polymer's content the hydrogel can shrink up to 30%. Addition of ethylene-bis-(oxyethylenenitrilo)-tetraacetic acid creates a gel, which is, on the one hand, easy to inject through a thin needle, and, on the other hand, has a shrinkage level under 10%, characteristic of a hydrogel with a greater dry residue content.

The hydrogel was used for the plasty of subcutaneous cellular tissue at the elimination of facial wrinkles. Hydrogel in the amount of 1 ml was injected to patient S., 47 years old. In the postoperative period the patient was observed for 12 months with regular examinations every three months. There were no inflammatory or allergic reactions. The desired cosmetic effect was achieved.

EXAMPLE 4

In order to produce the hydrogel we took 965 ml of twice-distilled pyrogen-free water with pH 5.6 and dissolved in it 28.7 g of acrylamide, 2.08 g of N,N'-methylene-bis-acrylamide, 3.5 g of N,N'-ethylene-bis-acrylamide, 0.1 g of poviargolum and 0.82 g of vinylpyrrolidone. This mixture was filtered as described in Example 1, and incubated at 60° C. for 12 hours. Then the gel was washed in 10 liters of water at 100° C. for 4.5 hours and again incubated for 1.5 hours at 120° C.

The hydrogel produced was sterilized by autoclaving as described in Example 1.

The substance had the following physical and chemical characteristics:

Appearance—colourless, semitransparent, opalescent gel;
Refraction index—1.352;
pH—5.2;
Density—1.0 g/cm3;
Content of monomers—0.04 ppm;
Bromation level—0.05(mg of bromine for 1l);
Bacteriostatic features: zone of bacteria's growth suppression—2.0 mm.

The hydrogel produced was used for the elimination of nasolabial folds. The hydrogel in the amount of 2 g was injected to patient K., 27 years old. In the postoperative period the patient was observed for 12 months with the regular examinations every three months. There was no inflammatory reaction or edema. The desired cosmetic effect was achieved.

Addition of vinylpyrrolidone into the mixture of cross-linking agents also allows production of a hydrogel, which is easy to inject through a thin needle and has a shrinkage rate of less than 10%, which is characteristic of the gel with a greater dry residue content.

EXAMPLE 5

In order to produce the hydrogel we took 375 ml of twice-distilled pyrogen-free water with pH 5.6 and dissolved in it 23.75 g of acrylamide, 1.075 g of N,N'-methylene-bis-acrylamide, 0.145 g of N,N'-ethylene-bis-acrylamide and 0.03 g of poviargolum. This solution was combined with 0.02 g of ammonium persulfate and 1 ml of 30% hydrogen peroxide. The mixture was filtered as described in Example 1, and incubated at 50° C. for 16 hours. Then the gel was washed in 3.5 liters of hot water at 100° C. for 4.0 hours and again incubated for 1 hour 130° C.

The hydrogel produced was sterilized by autoclaving as described in Example 1.

The substance has the following physical and chemical characteristics:

Appearance—colourless gel;
Refraction index—1.348;
pH—4.8;
Density—1.0 g/cm3;
Content of monomers—0.03 ppm;
Bromation level—0.12(mg of bromine for 1l);

Bacteriostatic features: zone of bacterial growth inhibition—2.0 mm.

The hydrogel produced was injected to patient L-ovaya, 36 years old, instead of a silicon prosthesis, which had been applied 3 years earlier for initial mammoplasty and which caused the fibrosis of both mammary glands 7 months after the operation. We conducted an operation to take out the silicon prosthesis with open capsulotomia injected 180 g of the hydrogel into each gland. 3 months later we injected 100 g more of the same hydrogel. In the postoperative period the patient was observed for 7 months with regular examinations every two months. There is no recurrence of the fibrosis. As a result of the operation, the mammary glands acquired the form and size, corresponding to the patient's constitution, and elasticity, characteristic for the tissue of a healthy mammary gland. The desired cosmetic effect was achieved.

Thus, the above-mentioned examples confirm that the offered biocompatible hydrogel can be obtained by the method disclosed.

The hydrogel of the present invention, provokes practically no tissue response, no sensitization of the organism, no dystrophic and necrotic changes. It can be used for endoprosthesis replacement and contour plasty of soft tissues as well as for endoprosthesis replacement of joints and as a synovial medium in joints and joint prostheses.

Compared to the well-known hydrogel-prototype (hydrogel "Formacryl"), the hydrogel of the present invention has a lower tissue response from the organism to the implantation, a higher stability of form during the implantation and a lower possibility of settling and proliferation of a pathogenic microorganisms within it.

The hydrogel of the present invention can be used as a filling stuff for endoprosthesis, which have a capsule and a filling stuff, as a depot for drugs during long-term pharmacotherapy, for example, during treatment of tumors and abscesses, and as a carrier for the cultivation of human and animal cells with a subsequent implantation of the hydrogel, containing the above-mentioned cells, into the organisms.

The introduction of additional cross-linking agents, such as 1-vinyl-2-pirrolydone and/or ethylene-bis-(oxyethylenenitrilo)-tetraacetic acid, into the hydrogel of the present invention, provides for diminishing its shrinkage without changing its other physical and mechanical characteristics.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

The invention claimed is:

1. A polyfunctional biocompatible hydrogel comprising:
   water; and
   a cross-linked copolymer comprising:
      acrylamide;
      N,N'-methylene-bis-acrylamide;
      N,N'-ethylene-bis-acrylamide; and
      poviargolum.

2. The polyfunctional biocompatible hydrogel of claim 1, wherein the cross-linked copolymer comprises:
   acrylamide ranging from 65.0 to 99.5 mass percent;
   N,N'-methylene-bis-acrylamide ranging from 0.2 to 6.5 mass percent;
   N,N'-ethylene-bis-acdrylamide ranging from 0.2 to 34.0 mass percent; and
   poviargolum ranging from 0.1 to 3.0 mass percent.

3. The polyfunctional biocompatible hydrogel of claim 1, wherein:
   acrylamide ranges from 1.3 to 15 mass percent;
   N,N'-methylene-bis-acrylamide ranges from 0.004 to 0.975 mass percent;
   N,N'-ethylene-bis-acrylamide ranges from 0.004 to 5.1 mass percent;
   poviargolum ranges from 0.002 to 0.45 mass percent; and
   water ranges up to 98.69 mass percent.

4. The polyfunctional biocompatible hydrogel of claim 1, wherein the copolymer further comprises a material selected from the group consisting of:
   a) vinylpyrrolidone;
   b) ethylene-bis-(oxyethylenenitrilo)-tetraacetic acid; and
   c) a combination of a) and b).

5. The polyfunctional biocompatible hydrogel of claim 4, wherein the cross-linked copolymer comprises:
   acrylamide ranging from 65.0 to 99.4 mass percent;
   N,N'-methylene-bis-acrylamide ranging from 0.2 to 6.5 mass percent;
   N,N'-ethylene-bis-acrylamide ranging from 0.2 to 34.0 mass percent;
   poviargolum ranging from 0.1 to 3.0 mass percent; and
   vinylpyrrolidone and/or ethylene-bis-(oxyethylenenitrilo)-tetraacetic acid ranging from 0.1 to 2.5 mass percent.

6. The polyfunctional biocompatible hydrogel of claim 4, wherein:
   acrylamide ranges from 1.3 to 15 mass percent;
   N,N'-methylene-bis-acrylamide ranges from 0.004 to 0.975 mass percent;
   N,N'-ethylene-bis-acrylamide ranges from 0.004 to 5.1 mass percent;
   poviargolum ranges from 0.002 to 0.45 mass percent;
   vinylpyrrolidone and/or ethylene-bis-(oxyethylenenitrilo)-tetraacetic acid ranges from 0.002 to 0.375 mass percent; and
   water ranges up to 98.688 mass percent.

7. The polyfunctional biocompatible hydrogel of claim 1 wherein the cross-linked copolymer makes up from 2.0 to 15.0 percent of a total mass of the biocompatible hydrogel.

8. The polyfunctional biocompatible hydrogel of claim 1, wherein the water is twice-distilled pyrogen-free water.

9. The polyfunctional biocompatible hydrogel of claim 1, wherein the hydrogel has a pH ranging from 3.5 to 7.5.

10. A method of producing a polyfunctional biocompatible hydrogel, comprising the steps of:
    a) mixing acrylamide with a cross-linking agent in an aqueous medium in the presence of a peroxide polymerization initiator;
    b) incubating the mixture of step a) at a temperature of 20 to 90° C. for 2 to 24 hours;
    c) further incubating the reagents at a temperature of 107 to 130° C. for a time less than or equal to two hours;
    wherein the cross-linking agent comprises N,N'-methylene-bis-acrylamide, N,N'-ethylene-bis-acrylamide, and poviargolum.

11. The method of claim 10, wherein the cross-linking agent further comprises a material selected from the group consisting of:
    a) vinylpyrrolidone;
    b) ethylene-bis-(oxyethylenenirtilo)-tetraacetic acid; and
    c) a combination of a) and b).

12. The method of claim 11, wherein a mixture of step a) comprises:
    acrylamide ranging from 1.3 to 15 mass percent;

N,N'-methylene-bis-acrylamide ranging from 0.004 to 0.975 mass percent;

N,N'-ethylene-bis-acrylamide ranging from 0.004 to 5.1 mass percent;

poviargolum ranging from 0.002 to 0.45 mass percent;

vinylpyrrolidone and/or ethylene-bis-(oxyethylenenitrilo)-tetraacetic acid ranging from 0.002 to 0.375 mass percent; and water ranging up to 98.688 mass percent.

13. The method of claim 10, further comprising, after step b), the step of washing the hydrogel in hot water.

14. The method of claim 13, wherein the hydrogel is washed in water of a temperature of 70 to 110° C. for at least 3 hours.

15. The method of claim 13, wherein the step of washing the hydrogel is carried out with a 1:8 to 1:10 ratio of the hydrogel to the water.

16. The method of claim 10, wherein the peroxide initiator comprises a solution including hydrogen peroxide and/or ammonium persulfate in an amount less than or equal to 0.3 mass percentage of a total weight of the original components.

17. The method of claim 10 wherein the aqueous medium comprises twice-distilled pyrogen-free water.

18. The method of claim 10 wherein:

a mixture of step a) comprises:

acrylamide ranging from 1.3 to 15 mass percent;

N,N'-methylene-bis-acrylamide ranging from 0.004 to 0.975 mass percent;

N,N'-ethylene-bis-acrylamide ranging from 0.004 to 5.1 mass percent;

poviargolum ranging from 0.002 to 0.45 mass percent; and water ranging up to 98.69 mass percent.

* * * * *